(12) United States Patent
Manzo (10) Patent No.: US 7,998,155 B2
(45) Date of Patent: Aug. 16, 2011

(54) METHOD AND APPARATUS FOR ANASTOMOSIS INCLUDING ANNULAR JOINING MEMBER

(75) Inventor: Scott Manzo, Shelton, CT (US)

(73) Assignee: Tyco Healthcare Group LP, Norwalk, CT (US)

(*) Notice: Subject to any disclaimer, the term of this patent is extended or adjusted under 35 U.S.C. 154(b) by 1421 days.

(21) Appl. No.: 10/518,040

(22) PCT Filed: Apr. 16, 2003

(86) PCT No.: PCT/US03/11693
§ 371 (c)(1),
(2), (4) Date: Dec. 9, 2004

(87) PCT Pub. No.: WO04/000093
PCT Pub. Date: Dec. 31, 2003

(65) Prior Publication Data
US 2005/0228411 A1 Oct. 13, 2005

(51) Int. Cl.
*A61B 17/08* (2006.01)
(52) U.S. Cl. .................................................. 606/155
(58) Field of Classification Search .................. 606/153, 606/155, 157, 158, 151, 152, 156; 132/273, 132/276, 277, 245, 252; 623/1.11, 1.12; 24/16 PB
See application file for complete search history.

(56) References Cited

U.S. PATENT DOCUMENTS

| 2,127,903 | A | | 8/1938 | Bowen |
| 3,683,940 | A | * | 8/1972 | Debue ........................... 132/262 |
| 4,553,543 | A | | 11/1985 | Amarasinghe |
| 4,803,984 | A | | 2/1989 | Narayanan et al. |
| 4,848,367 | A | | 7/1989 | Avant et al. |
| 4,911,164 | A | | 3/1990 | Roth |
| 4,957,499 | A | | 9/1990 | Lipatov et al. |
| 5,047,039 | A | | 9/1991 | Avant et al. |
| 5,122,156 | A | | 6/1992 | Granger et al. |
| 5,234,448 | A | | 8/1993 | Wholey et al. |

(Continued)

FOREIGN PATENT DOCUMENTS

WO 03/088848 10/2003

(Continued)

OTHER PUBLICATIONS

U.S. Appl. No. 10/516,437, entitled "Method and Apparatus for Anastomosis Including Annular Joining Member", filed Nov. 30, 2004.

(Continued)

*Primary Examiner* — Gary Jackson
*Assistant Examiner* — Michael G Mendoza (57) ABSTRACT

Apparatus and methods for performing a surgical anastomotic procedure are disclosed herein. Apparatus according to the present disclosure include a tubular body having a distal end and a proximal end and defining a longitudinal axis, the tubular body including an expandable anchor provided near the distal end thereof and an expandable cuff provided near the distal end of the tubular body and proximal of the expandable anchor, and a joining member (200) configured and adapted to be received about the expandable cuff of the tubular body, the joining member having an annular body portion (202) including a pair of opposed terminal edges (204, 206). The joining member has a retracted position in which the pair of opposed terminal edges overlap by a predetermined amount and an expanded position in which the pair of opposed terminal edges overlap by an amount less than the predetermined amount.

11 Claims, 8 Drawing Sheets

U.S. PATENT DOCUMENTS

| | | | |
|---|---|---|---|
| 5,403,333 A | 4/1995 | Kaster et al. | |
| 5,411,508 A | 5/1995 | Bessler et al. | |
| 5,425,739 A | 6/1995 | Jessen | |
| 5,464,414 A | 11/1995 | Cziffer | |
| 5,464,415 A | 11/1995 | Chen | |
| 5,478,353 A | 12/1995 | Yoon | |
| 5,486,187 A | 1/1996 | Schenck | |
| 5,540,701 A | 7/1996 | Sharkey et al. | |
| 5,545,171 A | 8/1996 | Sharkey et al. | |
| 5,549,619 A | 8/1996 | Peters et al. | |
| 5,554,162 A | 9/1996 | DeLange | |
| 5,569,272 A | 10/1996 | Reed et al. | |
| 5,578,044 A | 11/1996 | Gordon et al. | |
| 5,591,179 A | 1/1997 | Edelstein | |
| 5,591,206 A | 1/1997 | Moufarrège | |
| 5,695,504 A | 12/1997 | Gifford, III et al. | |
| 5,700,272 A | 12/1997 | Gordon et al. | |
| 5,702,412 A | 12/1997 | Popov et al. | |
| 5,707,380 A | 1/1998 | Hinchliffe et al. | |
| 5,713,889 A | 2/1998 | Chang | |
| 5,716,370 A | 2/1998 | Williamson, IV et al. | |
| 5,738,359 A * | 4/1998 | Gundy | 277/606 |
| 5,741,277 A | 4/1998 | Gordon et al. | |
| 5,797,934 A | 8/1998 | Rygaard | |
| 5,814,005 A | 9/1998 | Barra et al. | |
| 5,817,113 A | 10/1998 | Gifford, III et al. | |
| 5,833,698 A | 11/1998 | Hinchliffe et al. | |
| 5,868,762 A | 2/1999 | Cragg et al. | |
| 5,904,697 A | 5/1999 | Gifford, III et al. | |
| 5,944,730 A | 8/1999 | Nobles et al. | |
| 5,951,576 A | 9/1999 | Wakabayashi | |
| 5,980,483 A | 11/1999 | Dimitri | |
| 5,984,963 A * | 11/1999 | Ryan et al. | 623/1.11 |
| 6,024,748 A | 2/2000 | Manzo et al. | |
| 6,048,351 A | 4/2000 | Gordon et al. | |
| 6,048,360 A * | 4/2000 | Khosravi et al. | 623/1.11 |
| 6,051,007 A | 4/2000 | Hogendijk et al. | |
| 6,063,114 A | 5/2000 | Nash et al. | |
| 6,080,167 A | 6/2000 | Lyell | |
| 6,096,051 A | 8/2000 | Kortenbach et al. | |
| 6,149,658 A | 11/2000 | Gardiner et al. | |
| 6,152,455 A * | 11/2000 | Brockway et al. | 277/576 |
| 6,152,937 A | 11/2000 | Peterson et al. | |
| 6,171,319 B1 | 1/2001 | Nobles et al. | |
| 6,171,321 B1 | 1/2001 | Gifford, III et al. | |
| 6,176,864 B1 | 1/2001 | Chapman | |
| 6,203,553 B1 | 3/2001 | Robertson et al. | |
| 6,241,742 B1 | 6/2001 | Spence et al. | |
| 6,254,617 B1 | 7/2001 | Spence et al. | |
| 6,280,460 B1 | 8/2001 | Bolduc et al. | |
| 6,866,301 B2 * | 3/2005 | Brockway | 285/236 |

FOREIGN PATENT DOCUMENTS

| | | |
|---|---|---|
| WO | 04/000093 | 12/2003 |
| WO | 04/000134 | 12/2003 |
| WO | 04/000135 | 12/2003 |
| WO | 04/000136 | 12/2003 |
| WO | 2004/098418 | 11/2004 |

OTHER PUBLICATIONS

U.S. Appl. No. 10/517,404, entitled "Method and Apparatus for Anastomosis Including an Anchoring Sleeve", filed Dec. 7, 2004.

U.S. Appl. No. 10/514,774, entitled "Method and Apparatus for Anastomosis Including an Anchoring Sleeve", filed Nov. 17, 2004.

U.S. Appl. No. 10/514,140, entitled Method and Apparatus for Radical Prostatectomy Anastomosis, filed Nov. 9, 2004.

U.S. Appl. No. 10/516,434, entitled "Method and Apparatus for Anastomosis", filed Nov. 30, 2004.

* cited by examiner

METHOD AND APPARATUS FOR ANASTOMOSIS INCLUDING ANNULAR JOINING MEMBER

BACKGROUND

1. Technical Field

The present disclosure relates to apparatus and methods for anastomosing two hollow body parts and, more particularly to apparatus and methods for anastomosing a urethral stump of a patient to the bladder following a radical prostatectomy.

2. Background of Related Art

Anastomosis is the bringing together and/or joining of hollow or tubular structures. Most body conduits are generally cylindrical in configuration and have a circular cross-section. When it is desired to suture such a conduit, typically for attachment to another body conduit, sutures are placed around the circumference of the conduit in order to maintain the patency of its lumen or channel. This type of attachment is commonly referred to as an anastomosis. It can be appreciated that the sutures made on top of the conduit (i.e., on the side facing the surgeon) in an anastomosis are made relatively more easily than the sutures made underneath the conduit (i.e., on the side facing away from the surgeon).

The complexity of anastomosis attachment is made manifestly apparent in a surgical procedure referred to generally as a radical prostatectomy (i.e., a well established surgical procedure for patients with localized prostatic carcinoma). In general, radical prostatectomy procedures require the removal of cancerous tissue while preserving sexual function and continence in the patient. There are two primary types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, i.e., next to the external urethral sphincter. Next, the prostatic urethra is divided, the prostatic urethra and the prostate gland through which it goes are then pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and positioned against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult and complex. This difficulty is complicated by the tendency of the urethral stump to retract into adjacent tissue. As a result, considerable time and effort must be expended to re-expose the urethral stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179, issued to Edelstein, there is disclosed a suturing device including a shaft with portions defining an interior channel extending between a proximal and a distal end of the shaft. This channel includes a generally axial lumen which extends to the proximal end of the shaft and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164, issued to Roth, there is disclosed a suture guide with a curved distal portion. The distal portion of the suture guide has a plurality of exterior axial grooves which can be used to align and guide a curved needle and attached suture. In order to drive the urethral stump to an accessible position, the device is provided with a plurality of outwardly extendable members which engage the lumen of the urethra These members make it possible to push the urethral stump into approximation with the bladder neck.

In U.S. Pat. No. 5,047,039, issued to Avant et al., there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stump to the bladder neck easier. As such, each surgical procedure using prior art devices continues to be time consuming and requires great skill in order to be performed. Accordingly, the need exists for radical prostatectomy anastomosis devices which overcome the drawbacks of the prior art devices and which are quick and simple to use.

SUMMARY

Apparatus and methods for performing a surgical anastomotic procedure are disclosed herein. Apparatus according to the present disclosure include a tubular body having a distal end and a proximal end and defining a longitudinal axis, the tubular body including an expandable anchor provided near the distal end thereof and an expandable cuff provided near the distal end of the tubular body and proximal of the expandable anchor, and a joining member configured and adapted to be received about the expandable cuff of the tubular body, the joining member having an annular body portion including a pair of opposed terminal edges. The joining member has a retracted position in which the pair of opposed terminal edges overlap by a predetermined amount and an expanded position in which the pair of opposed terminal edges overlap by an amount less than the predetermined amount.

The expandable anchor has a first position in which the expandable anchor has a radius substantially equal to a radius of the tubular body and a second position in which the expandable anchor has a radius which is larger than the radius of the tubular body. The expandable cuff has a first position in which the expandable cuff has a radius substantially equal to a radius of the tubular body and a second position in which the expandable cuff has a radius which is larger than the radius of the tubular body.

The joining member includes at least one annular array of openings formed through the annular body portion. Each opening is preferably defined by a pair of opposed side walls transversely oriented with respect to the longitudinal axis, a longitudinally oriented angled proximal wall and a longitudinally oriented angled distal wall, wherein the proximal wall is angled such that an upper edge thereof is closer to the at least one tab than a lower edge thereof. The distal wall is desirably angled such that an upper edge thereof is closer to the at least one tab than a lower edge thereof.

The joining member includes at least one tab extending from a first of the pair of terminal edges of the annular body portion. The at least one tab is configured and adapted to be received within an opening of the at least one linear array of openings.

Preferably, each tab extends tangentially and distally from the first of the pair of terminal edges of the joining member and terminates in an angled terminal distal edge.

The joining member desirably includes a guide rail formed on an inner surface of the annular body portion along either side of the at least one array of openings. The guide rails are desirably arranged to slidably receive the at least one tab therebetween.

The joining member desirably includes a distal terminal edge, a proximal terminal edge, and a guide channel formed near a second of the pair of terminal edges of the annular body portion. The guide channel is defined by a pair of side walls extending radially inward from the distal and proximal terminal edges of the annular body. The guide channel is desirably further defined by an end wall interconnecting the terminal ends of the pair of side walls.

The joining member desirably includes a plurality of flanges extending radially outward from at least one of the distal and proximal terminal edges thereof. The joining member may include a plurality of projections formed along an outer surface of the annular body portion.

The joining member is preferably fabricated from a bio-absorbable material, a bio-compatible material or a shape memory alloy.

The joining member desirably includes a unidirectional coupling pair including at least one opening formed near a first of the pair of terminal edges and a plurality of projections formed along the outer surface of the annular body portion. The plurality of projections are configured and adapted to be received within the at least one opening to allow the joining member to go from the retracted position to the expanded position.

The apparatus further desirably includes a holder tube having a distal end and a proximal end. The holder tube is configured and adapted to be received about the tubular body and the joining member when in the retracted position.

The expandable cuff of the tubular body is desirably configured and adapted to press against an inner surface of the annular body portion of the joining member in order to expand the joining member from the retracted position to the expanded position.

A method for performing a surgical anastomosis is provided including the steps of providing an apparatus for performing an anastomotic procedure, the apparatus including a tubular body having a distal end and a proximal end, the tubular body including an expandable anchor provided near the distal end thereof and an expandable cuff provided near the distal end of the tubular body and proximal of the expandable anchor, and a joining member configured and adapted to be received about the expandable cuff of the tubular body, the joining member having an annular body portion including a pair of opposed terminal edge, wherein the joining member has a retracted position in which the pair of opposed terminal edges overlap by a predetermined amount and an expanded position in which the pair of opposed terminal edges overlap by an amount less than the predetermined amount.

The method further includes the steps of passing the apparatus through a body lumen and through an opening in a body vessel such that the expandable anchor of the tubular body is positioned within the body vessel, expanding the expandable anchor of the tubular body such that the expandable anchor of the tubular body has a radius which is larger than an opening of the body vessel, withdrawing the tubular body until the body vessel contacts a distal end of the body lumen, positioning the joining member over the expandable cuff at a location which extends between at least a portion of the body vessel and at least a portion of the body lumen, and expanding the expandable cuff of the tubular body against the inner surface of the joining member to expand the joining member against at least the portion of the body vessel and at least the portion of the body lumen to secure the joining member into position. The expandable anchor may be retracted, the expandable cuff may be retracted, and the tubular body may be withdrawn from the body vessel and body lumen.

It is contemplated that the surgical anastomosis is a radical prostatectomy, wherein the body vessel is the bladder and the body lumen is the urethra. The method further includes the step of removing the prostrate gland from between the urethra and the bladder to define a urethral stump and a bladder neck.

A radially expandable joining member is provided including an annular body portion defining a longitudinal axis, the annular body portion including a distal terminal edge, a proximal terminal edge and a first and a second side terminal edge, wherein each of the first and the second side terminal edges is longitudinally oriented, at least one annular array of openings formed in the annular body, and at least one locking tab extending tangentially from the first side terminal edge, each locking tab being in registration with a respective array of openings formed in the annular body and receivable in the openings of the at least one annular array of openings, wherein the joining member has a first position wherein the annular body has a first diameter and a second position wherein the annular body has a second diameter which is larger than the first diameter, wherein the at least one locking tab inhibits the annular body from returning to the first diameter, once expanded to the second diameter, by being received in an opening of the at least one array of openings.

The joining member includes two annular arrays of openings formed in the annular body and two tabs extending tangentially from the first side edge, wherein the two tabs are configured and dimensioned to be received, one each, within a respective opening formed in the annular body. The joining member further includes guide rails formed, one each, along each side of the two annular arrays of openings formed in the annular body.

The joining member further includes a guide channel formed near the second side terminal edge of the annular body. The guide channel is defined by a pair of side walls extending radially inward from the distal end proximal terminal edges of the annular body. The guide channel is further defined by an end wall interconnecting the terminal ends of the pair of side walls.

The joining member further includes a plurality of flanges extending radially outward from at least one of the distal and proximal terminal edges thereof.

These and other features of the apparatus and method disclosed herein, will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodi

DETAILED DESCRIPTION OF PREFERRED EMBODIMENTS

Preferred embodiments of the presently disclosed anastomosis apparatus will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Referring now to FIGS. 1-5, an anastomosis apparatus, in accordance with the principles of the present disclosure, is shown generally as reference numeral 100. Although apparatus 100 offers significant advantages to a radical prostatectomy procedure, it will be understood that the device is applicable for use in any anastomotic procedure where the end of a conduit is to be sutured to a hollow body organ.

Referring initially to FIGS. 14, a radially expandable joining member, in accordance with the present disclosure, is shown generally as reference numeral 200. Joining member 200 includes an annular body portion 202 having a substantially "C" shaped configuration, a first side terminal edge 204 and a second side terminal edge 206. It is envisioned that joining member 200 has a width defined by a distal terminal edge 208 and a proximal terminal edge 210.

Figure 1:
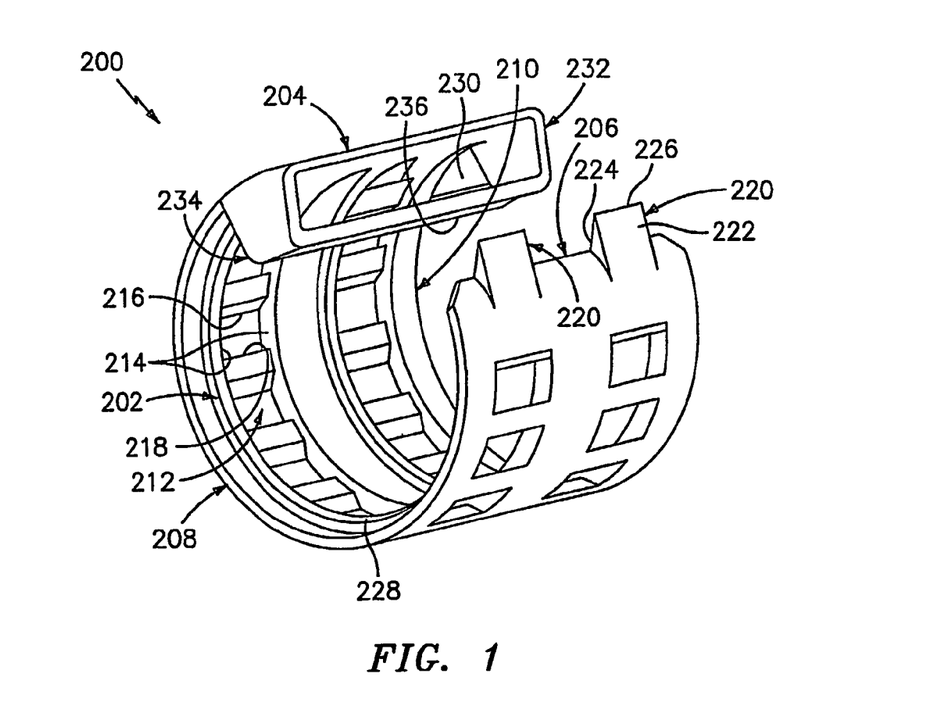
- FIG. 1 is a perspective view of an anastomotic radial joining member in accordance with an embodiment of the present disclosure.
Figure 2:
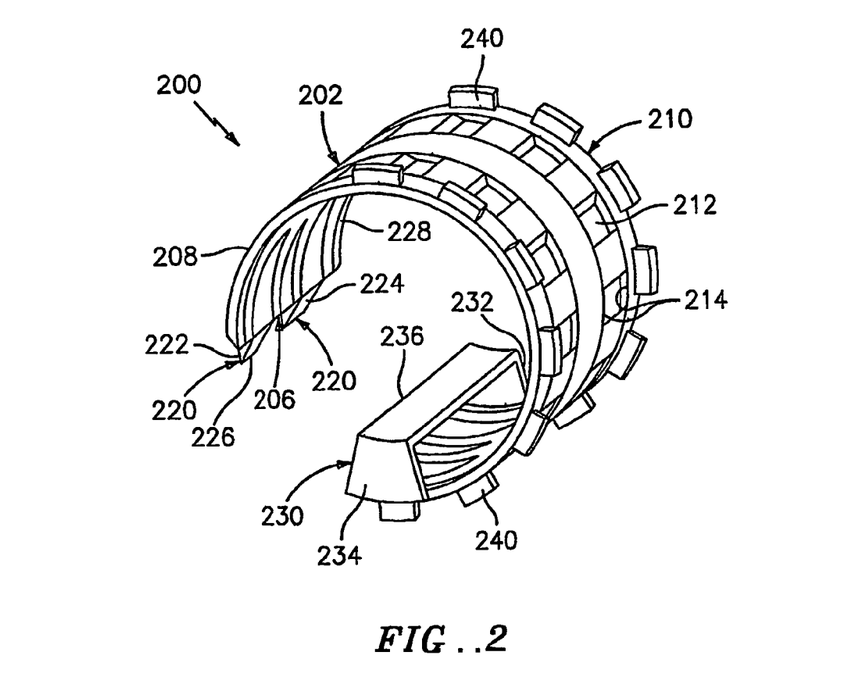
FIG. 2 is a perspective view of an anastomotic radial joining member in accordance with another embodiment of the present disclosure.
Figure 3:
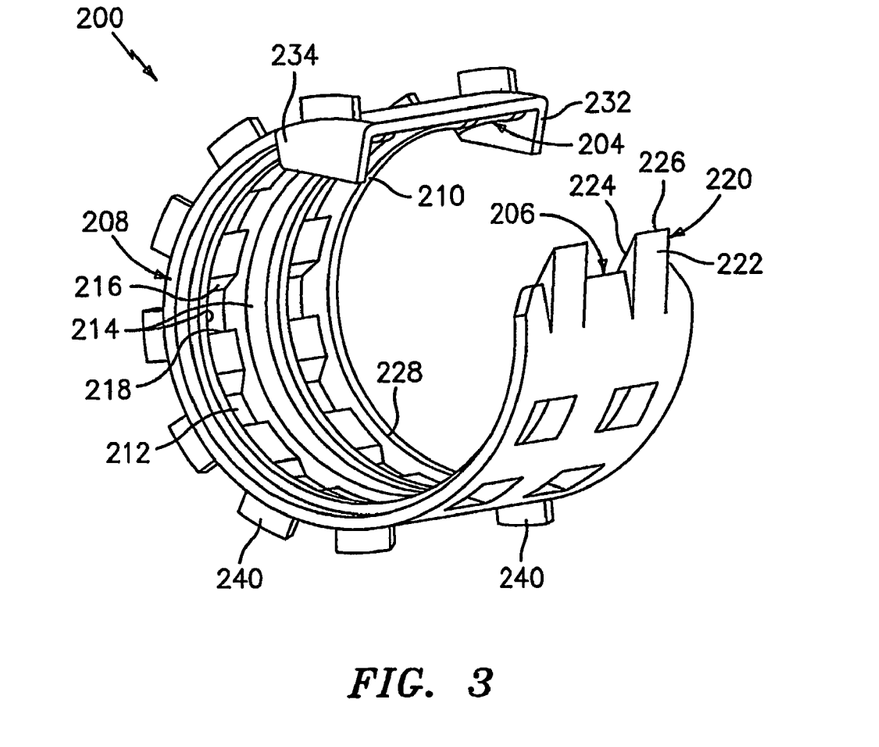
FIG. 3 is a perspective view of an anastomotic radial joining member in accordance with an alternative embodiment of the present disclosure.

Joining member 200 includes a first and a second annular array of openings 212 extending through annular body portion 202. Preferably, each of the first and second arrays is spaced from one another and parallel to distal and proximal terminal edges 208, 210. Preferably, each opening 212 is defined by a pair of side walls 214, a distal wall 216 and a proximal wall 218. More preferably, it is envisioned that distal wall 216 of each opening 212 is angled such that an upper edge of each distal wall 216 is closer to second side terminal edge 206 than a lower edge of each distal wall 216. It is further envisioned that proximal wall 218 of each opening 212 is closer to second side terminal edge 206 than an upper edge of each proximal wall 218. While a pair of arrays of openings 212 has been disclosed, it is envisioned that a single array or more than a pair of arrays of openings can be formed in annular body portion 202.

Joining member 200 further includes a pair of locking tabs 220 extending distally from second side terminal edge 206. In accordance with the present disclosure, each locking tab 220 is co-axially aligned with a respective array of openings 212. Preferably, each locking tab 220 includes an outer surface 222 which extends tangentially in a distal direction from the outer surface of annular body portion 202 from a location spaced a distance from second side terminal edge 206 of annular body portion 202. Each locking tab 220 further includes an angled inner surface 224 which extends from second side terminal edge 206 of annular body portion 202 and is oriented toward outer surface 222 of locking tab 220 in order to define a terminal edge 226 spaced a distance from second side terminal edge 206 of annular body portion 202. In accordance with the present disclosure, each locking tab 220 has a width which is less than a width of a respective opening 212. It is envisioned that joining member 200 is provided with a number of locking tabs 220 which are less than the number of arrays of openings 212.

It is contemplated that joining member 200 further includes a plurality of guide rails 228 formed on the inner surface of annular body portion 202 in order to define discrete channels therebetween. Preferably, a guide rail 228 is provided on either side of each array of openings 212 such that locking tabs 220 are slidably received therebetween.

Joining member 200 has an initial retracted position in which locking tabs 220 and second side terminal edge 206 overlap first side terminal edge 204, a predetermined selected amount, along an inner surface of annular body portion 202 (not shown). In this manner, locking tabs 220 overlie a respective array of openings 212 and are received between adjacent guide rails 228 formed on either side of opening 212. Joining member 200 has a subsequent expanded position in which locking tabs 220 and second terminal edge 206 overlap first side terminal edge 204, an amount less than the predetermined selected amount (not shown).

According to the present disclosure, when going from the retracted position to the expanded position, outer surface 222 of locking tabs 220 slide across and over angled distal walls 216 defining openings 212 of annular body portion 202. Accordingly, annular body portion 202 is permitted to expand radially outward upon the application of outwardly oriented radial forces applied to the inner surface thereof. In accordance with the present disclosure, locking tabs 220 in cooperation with openings 212 prevent the return of annular body portion 202 from the expanded position to the retracted position. In particular, when inwardly oriented radial forces are applied to the outer surface of annular body portion 202, terminal edge 226 of each locking tab 220 is received in a respective opening 212 such that angled inner surface 224 of locking tabs 220 slide along angled proximal wall 218 defining openings 212. Accordingly, as locking tabs 220 slide into respective openings 212, annular body portion 202 is stopped from retracting when second side terminal edge 206 contacts the inner surface of annular body portion 202.

As seen in FIG. 1, in accordance with an embodiment of the present disclosure, joining member 200 includes a guide channel 230 formed at first side terminal edge 204. Guide channel 230 is defined by a pair of side walls 232, 234 integrally formed with and extending radially inward from a respective distal and proximal terminal edge 208, 210 and an end wall 236 interconnecting side walls 232, 234. In accordance with the present disclosure, guide channel 230 is configured and adapted to receive locking tabs 220 and second terminal edge 206 therewithin when joining member 200 is in the retracted position. It is envisioned that side walls 232, 234 maintain second side terminal edge 206 aligned with first side terminal edge 204 and ensure that annular body portion 202 expands squarely. It is further envisioned that end wall 236 defining guide channel 230 inhibits locking tabs 220 and second side terminal edge 206 from becoming radially spaced from first side terminal edge 204.

As seen in FIG. 2, in accordance with an alternate embodiment of the present disclosure, joining member 200 further includes a plurality of discrete flanges 240 integrally formed along the outer surface of annular body portion 202. Preferably, flanges 240 are orthogonally oriented and are provided along both distal and proximal terminal edges 208, 210. In particular, flanges 240 preferably commence at first side terminal edge 204 of annular body portion 202 and terminate at a location spaced a distance from second side terminal edge 206. In this manner, second side terminal edge 206 can be received within guide channel 230 without interference from flanges 240.

As seen in FIG. 3, in accordance with yet another embodiment of the present disclosure, end wall 236 of guide channel 230 has been removed. Removal of end wall 236 from guide channel 230 of the embodiment of joining member 200 shown in FIG. 3 permits annular body portion 202 to be more easily expanded as compared to the embodiments shown in FIGS. 1 and 2.

In accordance with the present disclosure, it is contemplated that joining member 200 can be made from a medical grade material, such as, for example, stainless steel or titanium, however, it is preferred that joining member 200 is fabricated from a medical grade bio-absorbable material, such as, for example, polyglycolic acid (PGA) and/or polylactic acid (PLA). Preferably, joining member 200 is fabricated from a bio-absorable material which ensures that joining member 200 maintains its structural integrity for a predetermined period of time, such as, for example, approximately two weeks. It is further contemplated that joining member 200 can be fabricated from a shape memory alloy. Accordingly, joining member 200, fabricated from the shape memory alloy, would have an initial retracted configuration prior to implantation/insertion into position and an expanded configuration following implantation/insertion into position.

Figure 4:
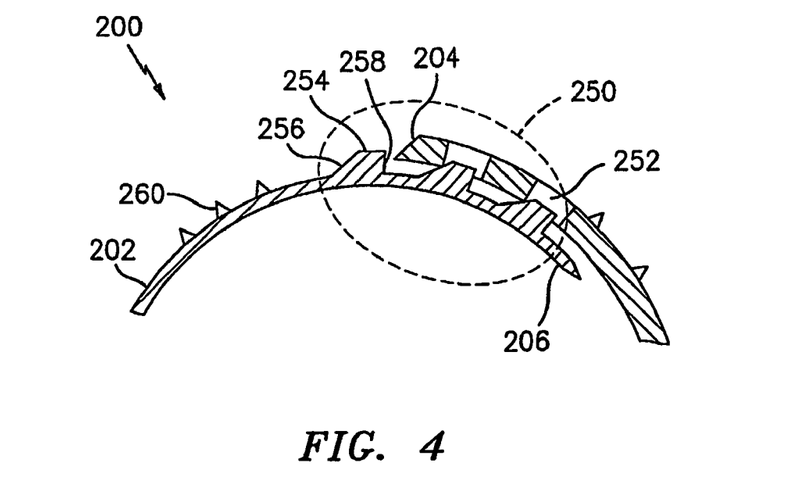
FIG. 4 is an enlarged cross sectional view of a locking mechanism for any of the radial joining members shown in FIGS. 1-3.

Turning now to FIG. 4, it is envisioned that any of joining members 200 shown in FIGS. 1-3 can be provided with a unidirectional barbed surf coupling pair 250. In particular, as seen in FIG. 4, coupling pair 250 includes at least one aperture 252 formed near first side terminal edge 204 of annular body portion 202 and a plurality of projections 254 formed along the outer surface annular body portion 202 near second side terminal edge 206. Each of the plurality of projections 254 is configured and adapted to be received and cooperate with aperture 252. In accordance with the present disclosure, each projection 254 includes a ramped distal surface 256 and an orthogonal proximal surface 258. Accordingly, provided second side terminal edge 206 of annular body portion 202 is in close proximity with the inner surface of annular body portion 202, joining member 200 is permitted to expanded by a camming effect created by ramped distal surface 256 of projections 254 against the distal surfaces of aperture 252 and restricted from retracting by a stopping effect created by orthogonal surface 258 of projections 254 against the proximal surfaces of aperture 252.

As seen in FIG. 4, the outer surface of annular body portion 202 of joining member 200 can be provided with a plurality of projections 260 extending therefrom. Preferably, projections 260 are spikes, however, it is envisioned that projections 260 can be transverse ribs, cones, pyramids, helical threads and the like.

Figure 5:
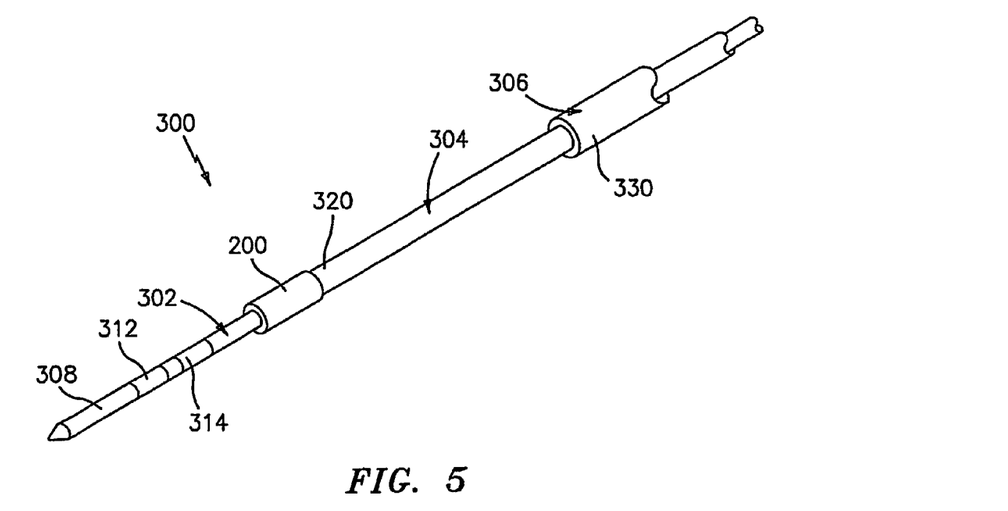
FIG. 5 is a perspective view of an insertion apparatus for any of the radial joining members shown in FIGS. 1-3.

Turning now to FIG. 5, an insertion tool for inserting joining member 200, in accordance with the principles of the present disclosure, is shown generally as reference numeral 300. Insertion tool 300 includes a tubular body 302, a holder tube 304 slidably received about tubular body 302 and a sleeve 306 slidably received about holder tube 304.

Tubular body 302 has a distal end 308, a proximal end (not shown) and defines a central lumen 310 therethrough. Tubular body 302 includes an expandable anchor 312 provided near distal end 308 of tubular body 302 and an expandable cuff 314 provided near distal end 308 of tubular body 302 and proximally of expandable anchor 312.

In a preferred embodiment, tubular body 302 includes a first inflation/deflation lumen (not shown) extending along the inner surface of central lumen 310 and is in fluid communication with expandable anchor 312 through at least one access opening formed in tubular body 302. Expandable anchor 312 has a first position in which expandable anchor 312 has a radius substantially equal to a radius of tubular body 302 and a second position in which expandable anchor 312 has a radius greater than the radius of tubular body 302. In use, the expandable anchor lumen is in fluid communication with a source of inflation fluid in order to inflate expandable anchor 312 from the first position to the second position.

In the preferred embodiment, tubular body 302 further includes a second inflation/deflation lumen (not shown) extending along the inner surface of central lumen 310 and is in fluid communication with expandable cuff 314 through at least one access opening formed in tubular body 302. Expandable cuff 314 has a first position in which expandable cuff 314 has a radius substantially equal to a radius of tubular body 302 and a second position in which expandable cuff 314 has a radius greater than the radius of tubular body 302. In use, the expandable cuff lumen is in fluid communication with a source of inflation fluid in order to inflate expandable cuff 314 from the first position to the second position.

Holder tube 304 has a distal end 320, a proximal end (not shown) and an axial lumen (not shown) extending therethrough. Axial lumen of holder tube 304 is dimensioned and sized to receive tubular body 302 therein. In accordance with the present disclosure, distal end 320 of holder tube 304 is configure and adapted to retain a joining member 200 thereon.

Sleeve 306 has a distal end 330, a proximal end (not shown) and an axial lumen (not shown) extending therethrough. Axial lumen of sleeve 306 is dimensioned and sized to receive holder tube 304 therein.

Preferably, expandable anchor 312 and expandable cuff 314 are fabricated from a medical grade polymer having suitable flexibility and structural integrity to withstand the forces associated with the inflation of anchor 312 and cuff 314 and with the function of withdrawing the hollow body organ and expanding joining member 200. While a fluid expandable anchor and cuff are described herein, it is envisioned that a mechanically expandable anchor and cuff can be provided, such as, for example, an onion sleeve or a double onion sleeve.

A preferred method of use and operation of anastomosis apparatus 100 in a radical anastomotic procedure will now be described in greater detail with reference to FIGS. 1-11 and in particular with reference to FIGS. 6-11. Apparatus 100 can be used in either the retropubic or the perineal prostatectomy approaches. With the prostate removed, the bladder neck "N" of the bladder "B" is first reconstructed by everting the inner mucosal lining of bladder "B" and suturing it down to the outer wall of bladder "B" using known surgical techniques. Likewise, urethral stump "S" of urethra "U" is reconstructed by everting the inner mucosal lining of urethral stump "S" and suturing it down to the outer wall of urethra "U", using known surgical techniques.

Preferably, with bladder neck "N" reconstructed, bladder neck "N" is sized to properly accommodate and retain distal end 308 of tubular body 302 within bladder "B" using a standard tennis racket type closure (i.e., the opening of the bladder neck constituting the head of the tennis racket and a radial incision extending from the bladder neck constituting the handle portion of the tennis racket. Most preferably, bladder neck "N" is sized to be approximately 7-8 mm in diameter.

With bladder neck "N" reconstructed, apparatus 100, including tubular body 302, joining member 200, holder tube 304 and sleeve 306, is passed trans-urethrally through urethra "U" until distal end 308 of tubular body 302 extends out of urethral stump "S" and into bladder "B" through bladder neck "N", as indicated by arrow "A" in FIG. 5. In particular, distal end 308 of tubular body 302 is preferably positioned such that expandable anchor 312 of tubular body 302 is positioned entirely within bladder "B".

Figure 6:
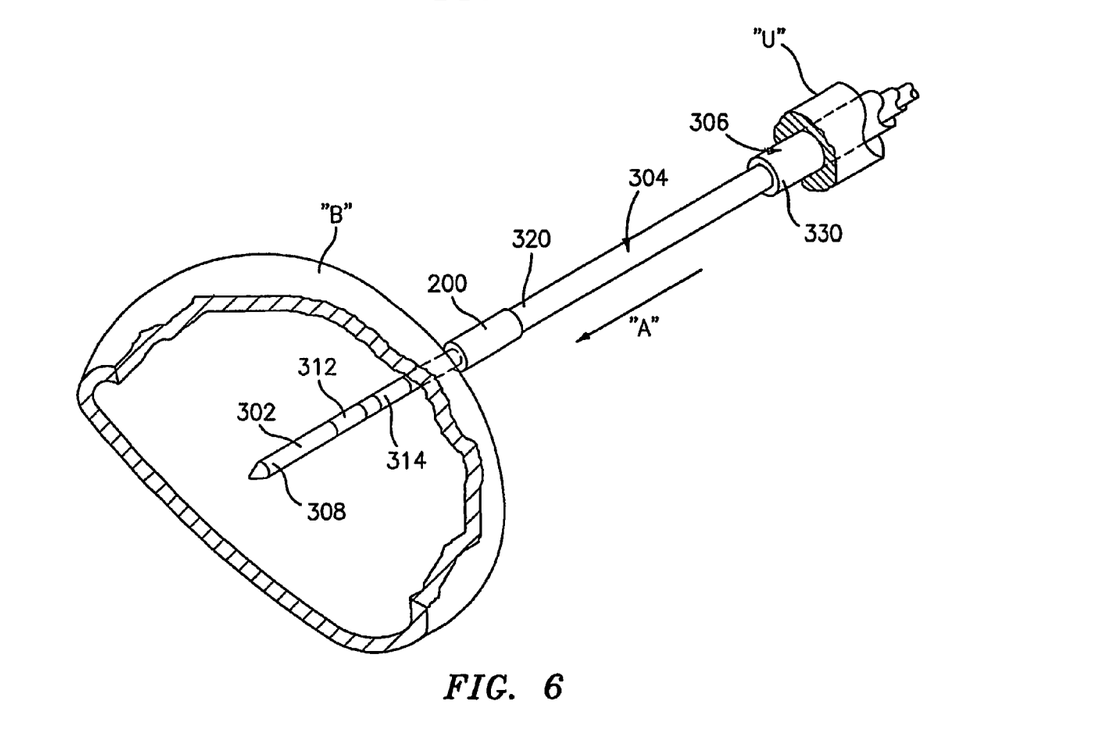
FIG. 6 is a partially broken away perspective view illustrating the passage of the insertion apparatus through a body lumen and into a hollow body organ.

With tubular body 302 positioned within bladder "B", as seen in FIG. S and 6, a fluid, i.e., air, carbon dioxide, saline or the like, is introduced through the expandable anchor lumen into expandable anchor 312 in order to thereby expand and inflate anchor 312. Inflation and expansion of anchor 312 will prevent tubular body 302 from being withdrawn from bladder "B".

Figure 7:
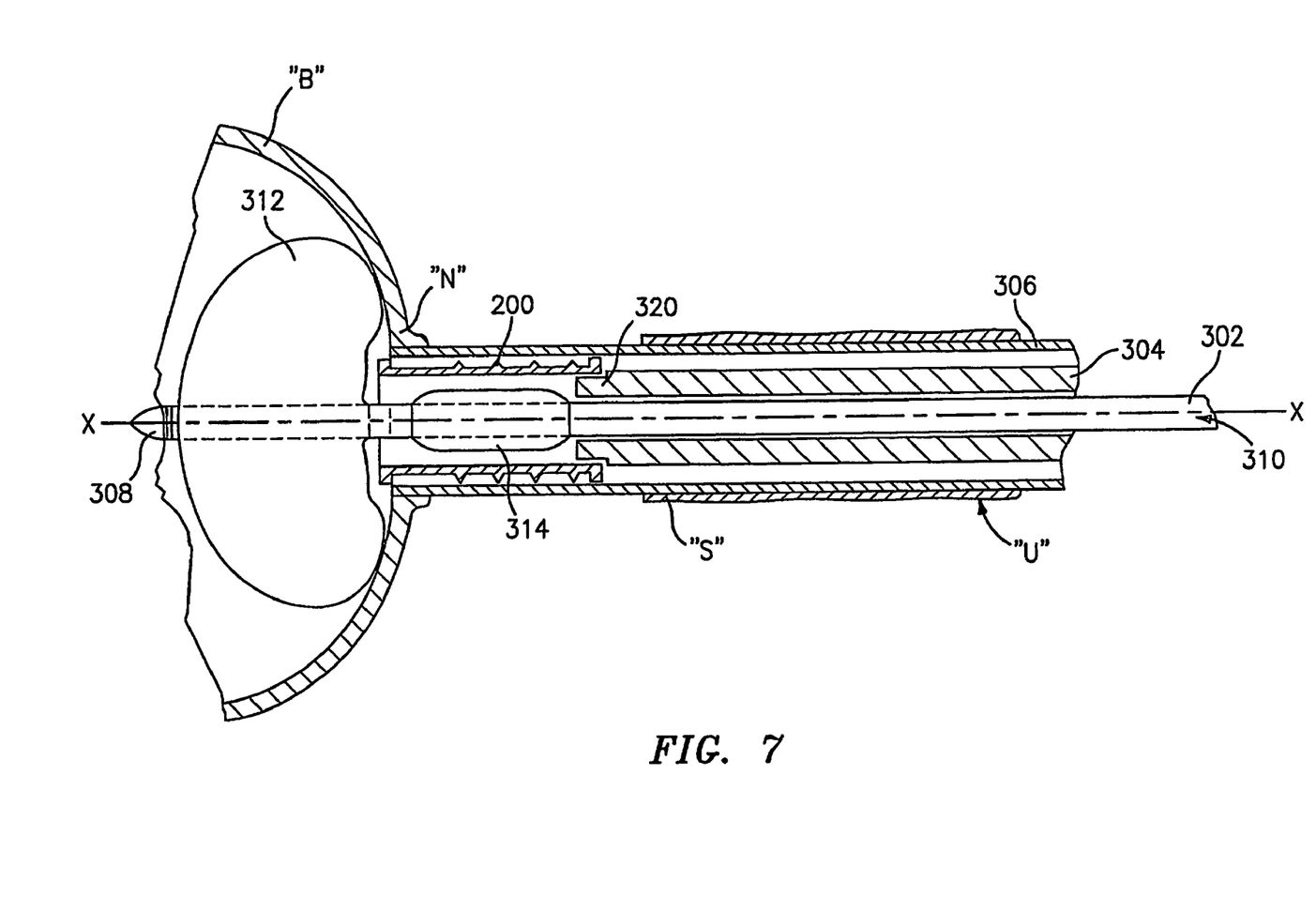
FIG. 7 is a cross-sectional side elevational view illustrating the positioning of the insertion tool and radial joining member as well as the expansion of a distal expansion member within the hollow body organ.
Figure 8:
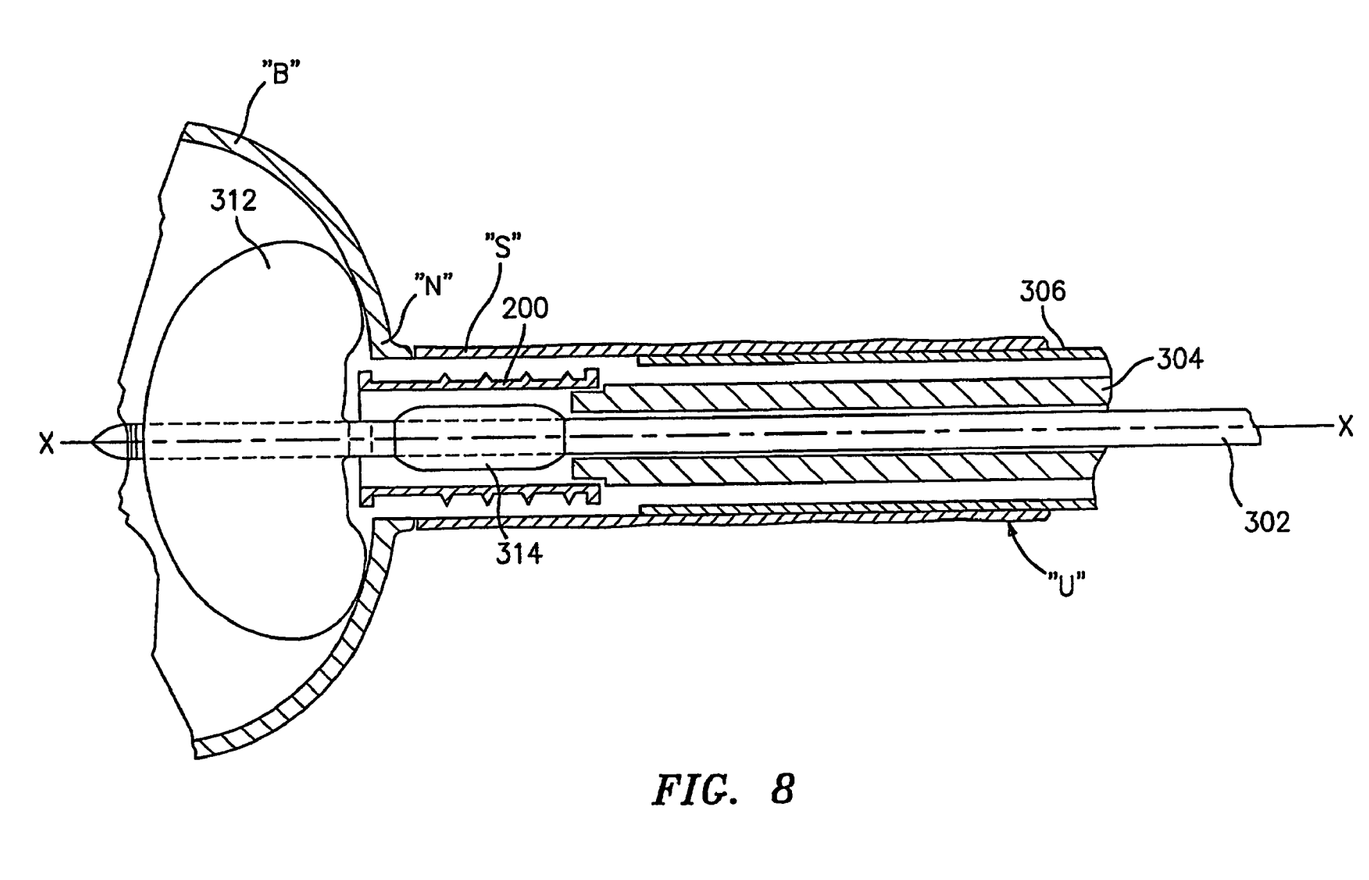
FIG. 8 is a cross-sectional side elevational view illustrating the approximation of the hollow body organ to the body lumen.

With anchor 312 in an expanded condition, tubular body 302 is withdrawn in a direction "C", opposite direction "A", as seen in FIG. 7. As tubular body 302 is withdrawn in direction "C", bladder "B" is also moved in direction "C" and approximated with urethral stump "S". Once bladder "B" has been approximated to urethral stump "S", holder tube 304, having a joining member 200 in the first retracted position and operatively coupled to distal end 320 thereof, is advanced distally through sleeve 306 until joining member 200 is positioned over expandable cuff 314. In accordance with the present disclosure, joining member 200 is positioned such that distal terminal edge 208 is within bladder "B" while proximal terminal edge 210 extends proximally of expandable cuff 314 and within urethra "U". Sleeve 306 is then withdrawn in a proximal direction.

Figure 9:
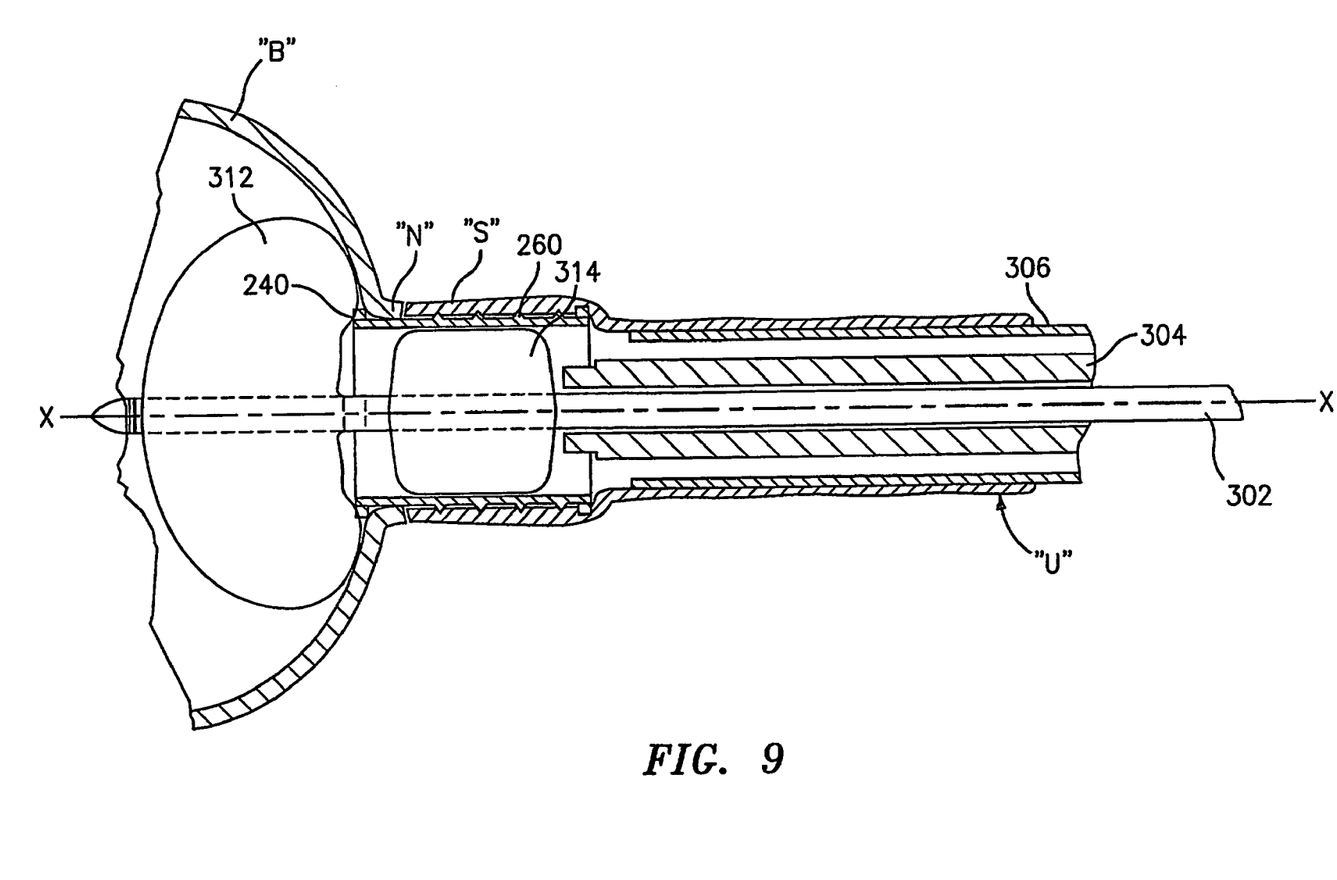
FIG. 9 is a cross-sectional side elevational view illustrating the expansion of a proximal expansion member within the radial joining member in order to anchor the radial joining member within the hollow body organ and the body lumen.
Figure 10:
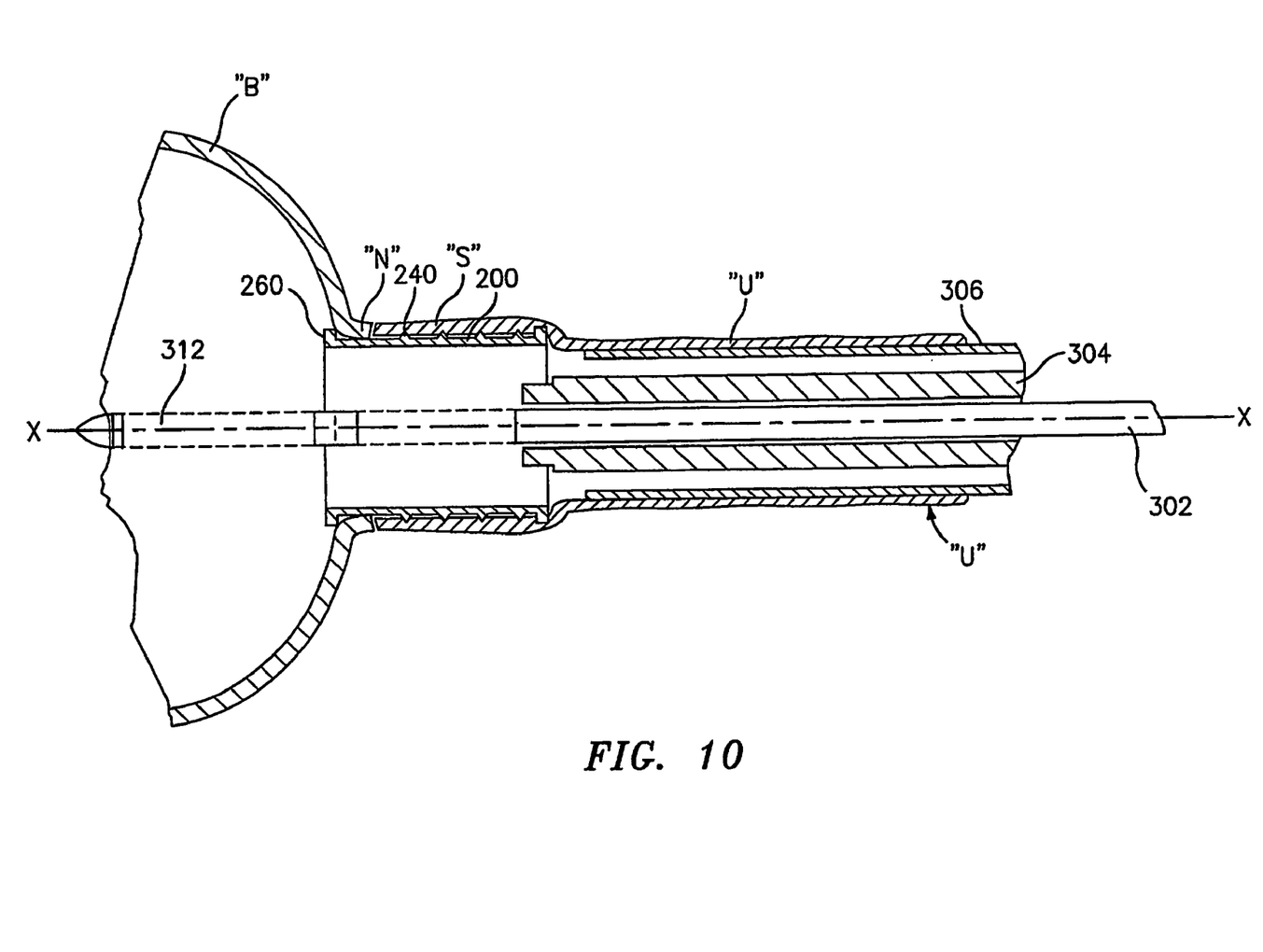
FIG. 10 is a cross-sectional side elevational view illustrating the retraction of distal and proximal expansion members and the radial joining member anchored in position between the hollow body organ and the body lumen.
Figure 11:
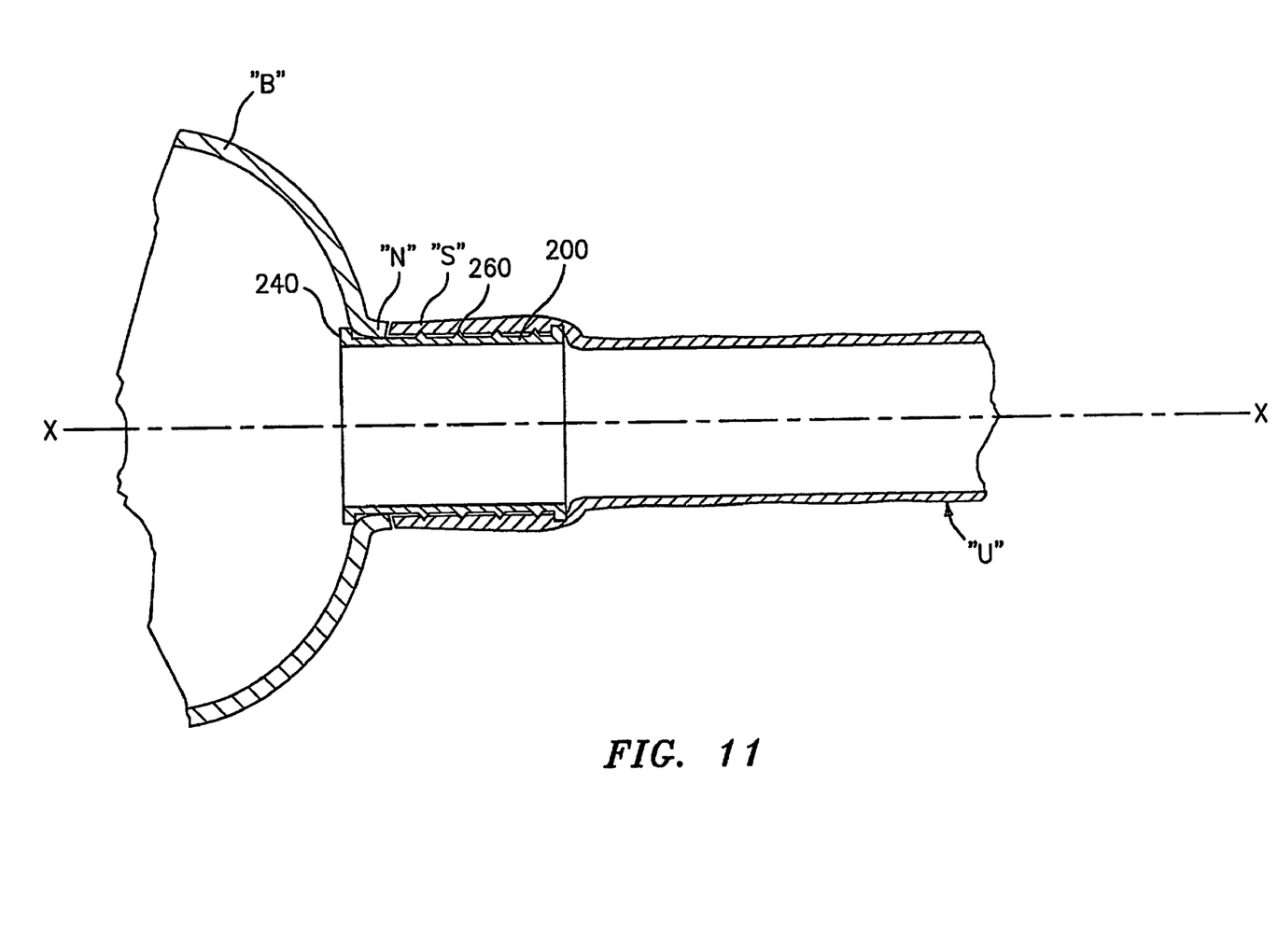
FIG. 11 is a cross-sectional side elevational view illustrating the final anastomosed hollow body organ and body lumen with the radial joining member anchored in position.

As seen in FIG. 9, with sleeve 306 withdrawn, a fluid, i.e., air, carbon dioxide, saline or the like, is introduced through expandable cuff inflation/deflation lumen into expandable cuff 314 to thereby expand and inflate cuff 314 into contact with the inner surface of joining member 200. Inflation of expandable cuff 314 results in the radial expansion of joining member 200, from the first retracted position to the second expanded position, and in turn the pressing of the outer surface of joining member 200 against the inner surface of urethra "U" and into bladder neck "N", thus anchoring bladder "B" to urethra "U". As seen in FIG. 10, expandable anchor 302 and expandable cuff 314 are retracted and, as seen in FIG. 11, tubular body 302, holding tube 304 and sleeve 306 are withdrawn from within bladder "B" and urethra "U".

In accordance with the present disclosure, as bladder neck "N" and urethral stump "S" constrict in diameter about joining member 200, i.e., applies a radially inward oriented constriction force about the outer surface of annular body portion 202, tabs 220 will enter into and engage openings 212 formed in annular body portion 202 and lock joining member 200 in the expanded position within bladder neck "N" and urethral stump "S". As described in greater detail above, as annular body portion 202 is constricted, locking tabs 220 slide into and engage respective openings 212 formed in annular body portion 212 until second side terminal edge 206 of annular body portion 202 contacts the guide rails 228 formed along the inner surface of annular body portion 202.

Preferably, if a joining member 200 having flanges 240 is used in the anastomotic procedure, as seen in FIGS. 7-11, flanges 240 formed along distal terminal edge 208 are positioned within bladder neck "N" so that after expansion of joining member 200, flanges 240 contact the inner surface of bladder neck "N" and inhibit withdrawal of joining member 200 therefrom. Further, if a joining member 200 having a plurality of projections 260, i.e., spikes, formed along the outer surface of the annular body wall 202 is used in the anastomotic procedure, as seen in FIGS. 7-11, the spikes will dig into the surface of bladder neck "N" and urethra "U" in order to inhibit separation of bladder neck "N" from urethral stump "S".

The expandable anchor for engaging a body vessel may comprise any expandable structure, including those disclosed in certain embodiments of the following PCT Applications, all filed on an even date herewith: application entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including An Expandable Anchor, invented by Russell Heinrich and Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Anchoring Sleeve, invented by Scott Manzo; the disclosures of which are all hereby incorporated by reference herein, in their entirety.

The joining member for joining body vessels may comprise any joining member, including those disclosed in certain embodiments of the following PCI Applications, all filed on an even date herewith: application entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including An Anchor For Engaging A Body Vessel And Deployable Sutures, invented by Scott Manzo; Method And Apparatus For Anastomosis Including An Anchoring Sleeve, invented by Scott Manzo; Method And Apparatus For Anastomosis Including An Expandable Anchor, invented by Russell Heinrich and Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Anchoring Sleeve, invented by Scott Manzo; the disclosures of which are all hereby incorporated by reference herein, in their entirety.

The methods and apparatus disclosed herein may be used for approximating and/or joining the urethra and bladder, intestinal portions of the body, blood vessels or any other body vessels.

Although the illustrative embodiments of the present disclosure have been described herein with reference to the accompanying drawings, it is to be understood that the disclosure is not limited to these embodiments, and that various other changes and modifications may be affected therein by one skilled in the art without departing from the scope or spirit of the disclosure. All such changes and modifications are intended to be included within the scope of the appended claims.

What is claimed is:

1. A radially expandable joining member for joining body vessels, comprising:
   an annular body portion defining a longitudinal axis, the annular body portion including a distal terminal edge, a proximal terminal edge and a first and a second side terminal edge, wherein each of the first and the second side terminal edges is longitudinally oriented;
   a guide channel formed near the first side terminal edge of the annular body;
   at least one annular array of openings formed in the annular body;
   at least one locking tab including an outer surface extending tangentially from an outer surface of the annular body portion, and extending radially outward from the first side terminal edge, each locking tab being in registration with a respective array of openings formed in the annular body and receivable in the openings of the at least one annular array of openings, wherein the joining member has a first position wherein the annular body has a first diameter and the second side terminal edge overlaps the first side terminal edge such that the outer surface of the at least one locking tab lies against an inner surface of the annular body, and a second position wherein the annular body has a second diameter which is larger than the first diameter, wherein the outer surface of the at least one locking tab slides over and across the openings of the at least one array of openings to permit the annular body to move to the second position when a radially outward force is applied to the inner surface of the annular body portion, and wherein the at least one locking tab inhibits the annular body from returning to the first diameter when the body vessels apply a radially inward oriented constriction force about an outer surface of the annular body portion, by being received in an opening of the at least one array of openings ; and
   a pair of guide rails extending radially inward from an inner surface of the annular body portion, at least one of the pair of guide rails being spaced a longitudinal distance from each of the proximal and distal terminal edges and extending circumferentially a substantial length of the at least one annular array of openings such that the at least one locking tab is slidably received between the pair of guide rails.

2. The joining member according to claim 1, including two annular arrays of openings formed in the annular body and two tabs extending tangentially from the first side edge, wherein the two tabs are configured and dimensioned to be received, one each, within a respective opening formed in the annular body.

3. The joining member according to claim 2, wherein the guide rails are formed, one each, along each side of the two annular arrays of openings formed in the annular body.

4. The joining member according to claim 1, wherein the guide channel is defined by a pair of side walls extending radially inward from the distal end proximal terminal edges of the annular body.

5. The joining member according to claim 4, wherein the guide channel is further defined by an end wall interconnecting the terminal ends of the pair of side walls.

6. The joining member according to claim 5, further including a plurality of flanges extending radially outward directly from at least one of the distal and proximal terminal edges thereof.

7. A radially expandable joining member, comprising:
   an annular body portion defining a longitudinal axis, the annular body portion including a distal terminal edge, a proximal terminal edge and a first and a second side terminal edge, wherein each of the first and the second side terminal edges is longitudinally oriented;
   at least one annular array of openings formed in the annular body;
   at least one locking tab extending both tangentially and radially beyond the first side terminal edge, each locking tab being in registration with a respective array of openings formed in the annular body and receivable in the openings of the at least one annular array of openings, wherein the joining member has a first position wherein the annular body has a first diameter and the second side terminal edge overlaps the first side terminal edge such that an outer surface of the at least one locking tab lies against an inner surface of the annular body, and a second position wherein the annular body has a second diameter which is larger than the first diameter, wherein the outer surface of the at least one locking tab slides over and across the openings of the at least one array of openings to permit the annular body to expand from the first diameter to the second diameter when a radially outward force is applied to the inner surface of the annular body portion, and wherein the at least one locking tab inhibits the annular body from returning to the first diameter, once expanded to the second diameter, by being received in an opening of the at least one array of openings; and
   a pair of guide rails extending radially inward from an inner surface of the annular body portion, at least one of the pair of guide rails being spaced a longitudinal distance from each of the proximal and distal terminal edges and extending circumferentially a substantial length of the at least one annular array of openings such that the at least one locking tab is slidably received between the pair of guide rails.

8. The joining member according to claim 7, wherein each of the openings of the at least one annular array of openings is defined by an angled wall such that an upper edge of the angled wall is closer to the second side terminal edge than a lower edge of the angled wall.

9. The joining member according to claim 7, wherein the joining member is fabricated from a bio-absorbable material.

10. The joining member according to claim 7, wherein the joining member is fabricated from a shape memory alloy.

11. The joining member according to claim 7, wherein the joining member includes a plurality of projections formed along an outer surface of the annular body portion.

* * * * *